United States Patent [19]

Coe et al.

[11] Patent Number: 5,074,856

[45] Date of Patent: * Dec. 24, 1991

[54] THREE-DIMENSIONAL SHAPED ABSORBENT ARTICLE WITH A BICOMPONENT BAFFLE

[75] Inventors: Louise C. Coe, Appleton; Anne M. Fahrenkrug, Oshkosh; Julie T. Brocker; James D. Milner, both of Appleton, all of Wis.

[73] Assignee: Kimberly-Clark Corporation, Neehah, Wis.

[*] Notice: The portion of the term of this patent subsequent to Sep. 13, 2005 has been disclaimed.

[21] Appl. No.: 471,917

[22] Filed: Jan. 29, 1990

Related U.S. Application Data

[63] Continuation-in-part of Ser. No. 45,344, May 1, 1987, abandoned, which is a continuation of Ser. No. 818,438, Jan. 13, 1986, abandoned.

[51] Int. Cl.⁵ .............................................. A61F 13/18
[52] U.S. Cl. ................................... 604/385.1; 604/370; 604/385.2
[58] Field of Search ................ 604/385.1, 370, 385.2, 604/367

[56] References Cited

U.S. PATENT DOCUMENTS

| | | | |
|---|---|---|---|
| 3,371,668 | 3/1968 | Johnson | 128/290 |
| 3,639,917 | 2/1972 | Althouse | 2/270 |
| 3,779,246 | 12/1973 | Mesek et al. | 128/287 |
| 3,819,401 | 6/1974 | Massengale et al. | 156/85 |
| 3,912,565 | 10/1975 | Koch et al. | 156/85 |
| 4,333,782 | 8/1982 | Pieniak | 156/164 |
| 4,397,644 | 8/1983 | Matthews et al. | 604/378 |
| 4,433,972 | 2/1984 | Malfitann | 604/385 |
| 4,490,147 | 12/1984 | Pierce et al. | 604/378 |
| 4,579,556 | 4/1986 | McFarland | 604/385 A |
| 4,641,381 | 2/1987 | Heran et al. | 2/400 |
| 4,668,230 | 3/1987 | Damico et al. | 604/385 A |
| 4,681,793 | 7/1987 | Linman et al. | 428/138 |
| 4,701,177 | 10/1987 | Ellis et al. | 604/385 A |
| 4,704,107 | 11/1987 | Coates | 604/357 |
| 4,770,657 | 9/1988 | Ellis et al. | 604/385 A |
| 4,772,282 | 9/1988 | Oakley | 604/385.1 |

FOREIGN PATENT DOCUMENTS

| | | |
|---|---|---|
| 0091412 | 10/1983 | European Pat. Off. . |
| 0139484 | 5/1985 | European Pat. Off. . |
| 0164435 | 12/1985 | European Pat. Off. . |
| 2142241 | 1/1985 | United Kingdom . |
| 2142541 | 1/1985 | United Kingdom . |
| 2156681 | 1/1988 | United Kingdom . |

Primary Examiner—Stephen C. Pellegrino
Assistant Examiner—Gary Jackson
Attorney, Agent, or Firm—Thomas J. Connelly

[57] ABSTRACT

An absorbent article is disclosed for absorbing and retaining human exudate. The article includes a liquid permeable bodyside liner, a baffle and an absorbent positioned therebetween. The baffle is constructed of a liquid-impermeable inner layer and a cloth-like outer layer. The baffle and liner are joined together about their outer peripheries to enclose the absorbent. The absorbent has an hourglass shape with enlarged end portions separated by a narrow center portion. A pair of walls are formed on opposite sides of the center portion of the absorbent by securing an elastic strip between the liner and the baffle. The walls extend upward and outward from the center portion and are separated by a distance approximately equal to the width of one of the end portions. The upstanding walls prevent side leakage of body fluid, especially during periods of high fluid flow.

14 Claims, 4 Drawing Sheets

THREE-DIMENSIONAL SHAPED ABSORBENT ARTICLE WITH A BICOMPONENT BAFFLE

This application is a continuation-in-part of copending U.S. patent application Ser. No. 07/045,344 filed May 1, 1987, which is a continuation of U.S. patent application Ser. No. 06/818,438, filed Jan. 13, 1986, now abandoned.

FIELD OF THE INVENTION

This invention relates to a three-dimensional shaped absorbent article, such as a sanitary napkin, having a bicomponent baffle. More particularly, it relates to a sanitary napkin having a baffle constructed of a liquid-impermeable inner layer and a cloth-like outer layer.

BACKGROUND OF THE INVENTION

Leakage of body fluid from the sides of sanitary napkins, feminine pads, panty liners, diapers, incontinent garments, etc. is a problem especially during periods of heavy flow. One reason for side leakage is that the body fluid, for example: menses, blood, catamenial fluids and urine, can not be absorbed fast enough by the absorbent and therefore will pool on the liquid permeable cover. This liquid is then transported to the sides of the product which are the closest peripheral edges to the fluid. The fluid movement can also be facilitated by the convex shape of the cover and by any creases which may form in the cover due to the wearer's anatomy and body movement. Side leakage can also be influenced by the thinnest of the product since thin products do not conform to the anatomy of the wearer as well as thicker products.

Many new products have been made with the goal of solving side leakage. Success has been achieved by products which closely follow the shape of the body and have their greatest absorption capacity where the need is greatest. U.S. Pat. Nos. 4,770,657, 4,701,177, 4,579,556, 4,668,230 and 4,772,282 present shaped feminine products which utilize side flaps or wings adjacent to the longitudinal side edges to prevent side leakage. Other embodiments are taught in foreign patents GB 2,156,681, GB 2,142,241, GB 2,142,541, EP 0,091,412, EP 0,164,435 and EP 0,139,484.

With the use of these body conforming products, there has been voiced a concern that the baffle sometimes irritates the inner thighs. Several U.S. Pat. Nos., including 3,779,246, 4,641,381, 4,681,793 and 4,704,107 teach baffles constructed of inner and outer layers so as to provide a soft feel against the wearer's skin and a liquid-impermeable layer to hold in the body fluids. However, these dual layer baffles have only been used with relatively flat products.

Now, a new bicomponent baffle has been incorporated into a three-dimensional shaped absorbent article to provide superior protection against side leakage while also providing a soft feel against the wearer's thighs.

SUMMARY OF THE INVENTION

Briefly, the present invention relates to a three-dimensional shaped absorbent article, such as a sanitary napkin, feminine pad, panty liner, diaper or incontinent garment, which has a liquid permeable bodyside liner, a baffle and an absorbent positioned therebetween. The baffle is constructed of a liquid-impermeable inner layer and a cloth-like outer layer. The baffle and liner are bonded together about their outer peripheries to enclose the absorbent. The absorbent has an hourglass shape with enlarged end portions seperated by a narrow center portion. A pair of walls are formed on opposite sides of the center portion of the absorbent by securing an elastic strip between the liner to the baffle. The walls extend upward and outward from the center portion and are seperated by a distance approximately equal to the width of one of the end portions. The upstanding walls prevent side leakage of body fluid, especially during periods of high fluid flow.

The general object of this invention is to provide a three-dimensional shaped absorbent article which can prevent side leakage of body fluid as well as exhibit a soft, cloth-like feel against the wearer's thighs. A more specific object of this invention is to provide a body conforming sanitary napkin having a bicomponent baffle.

Another object of this invention is to provide catamenial and incontinent devices with improved protection against side leakage.

Still, another object of this invention is to provide a low cost absorbent article which prevents side leakage and is comfortable to wear.

Still further, an object of this invention is to provide a catamenial product which utilizes a baffle having a liquid-impermeable inner layer and a cloth-like outer layer.

Other objects and advantages of the present invention will become more apparent to those skilled in the art in view of the following description and the accompanying drawings.

DETAILED DESCRIPTION OF THE PREFERRED EMBODIMENT

Referring to FIGS. 1-7, an absorbent article 10, such as a sanitary napkin, feminine pad, panty liner, diaper or incontinent garment, is shown constructed of a liquid permeable bodyside liner 12, a baffle 14 and an absorbent 16. The liner 12 and the baffle 14 are bonded together to enclose the absorbent 16, best shown in FIG. 7.

The bodyside liner 12 may be any suitable fluid permeable material. Typical of such materials are nonwovens, tissues, perforated polymer sheets, and composites thereof. A spunbonded polypropylene web bonded to a layer of staple fibers of polyester or polypropylene is a composite which makes a good bodyside liner since it exhibits a cushioned feel. Another suitable composite material for the bodyside liner 12 is taught in U.S. Pat. No. 4,397,644, which is incorporated by reference and made a part hereof.

Figure 1:
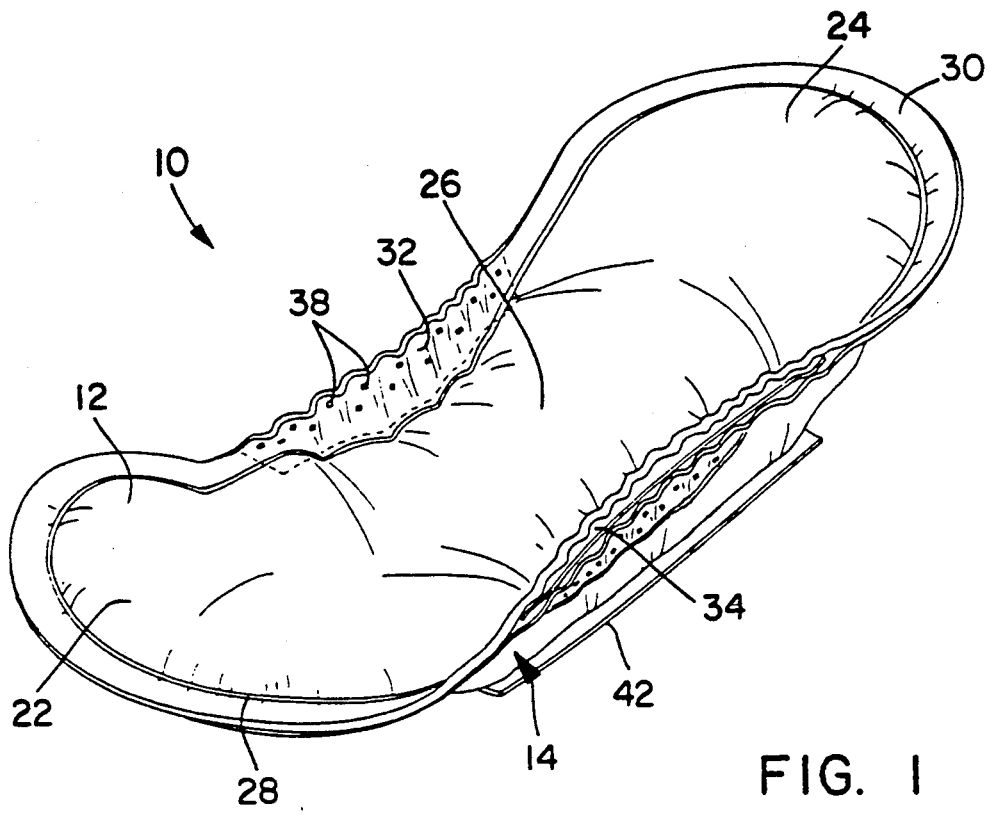
FIG. 1 is a perspective view of an absorbent article in accordance with this invention.
Figure 2:
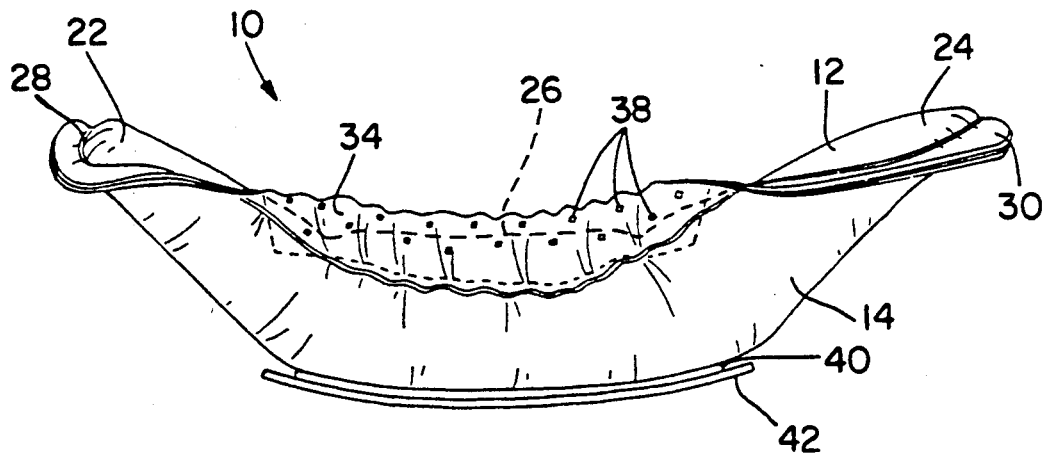
FIG. 2 is a side view of the absorbent article shown in FIG. 1.
Figures 3, 4:
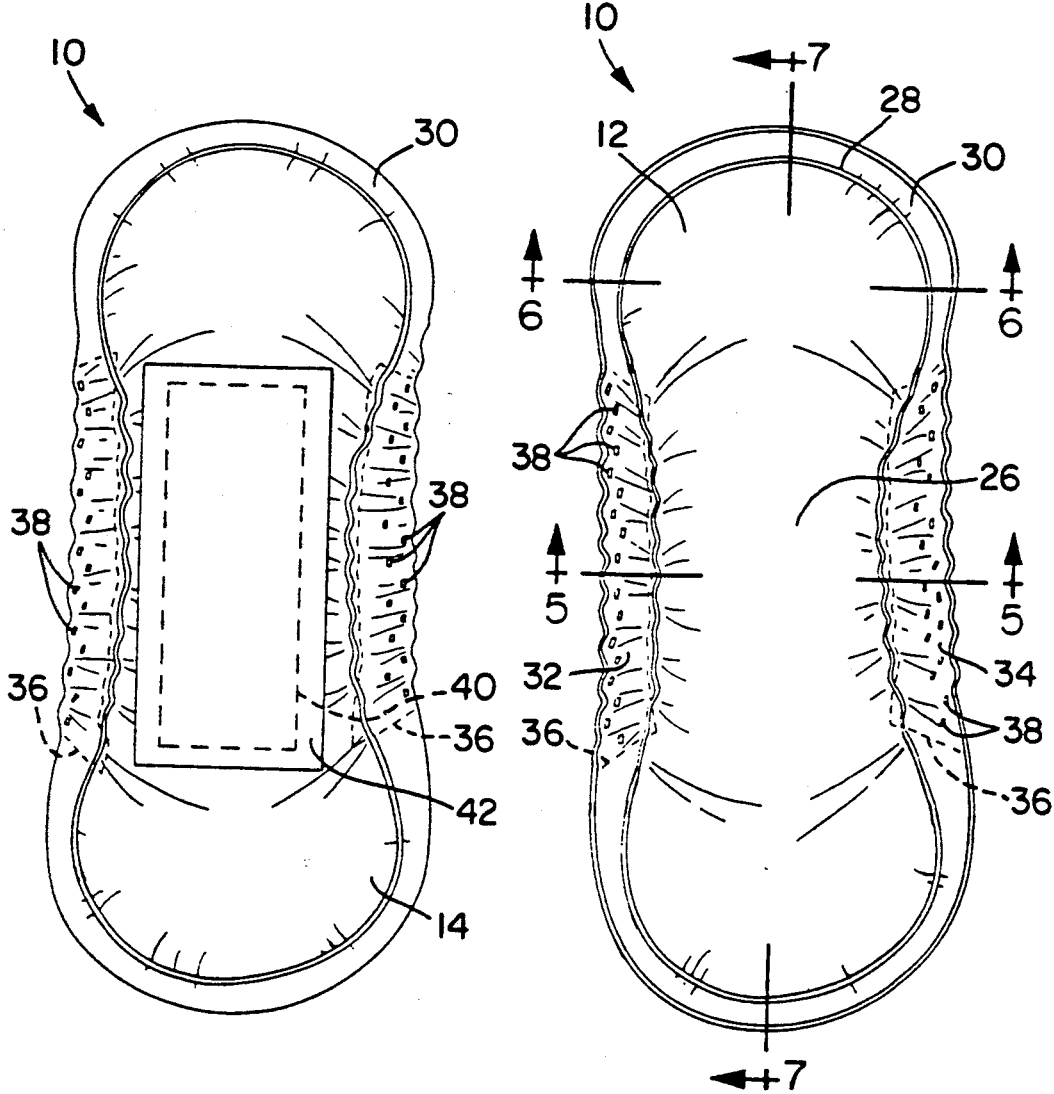
FIG. 3 is the bottom view of the absorbent article shown in FIG. 1.
FIG. 4 is the top view of the absorbent article shown in FIG. 1.
Figure 5:
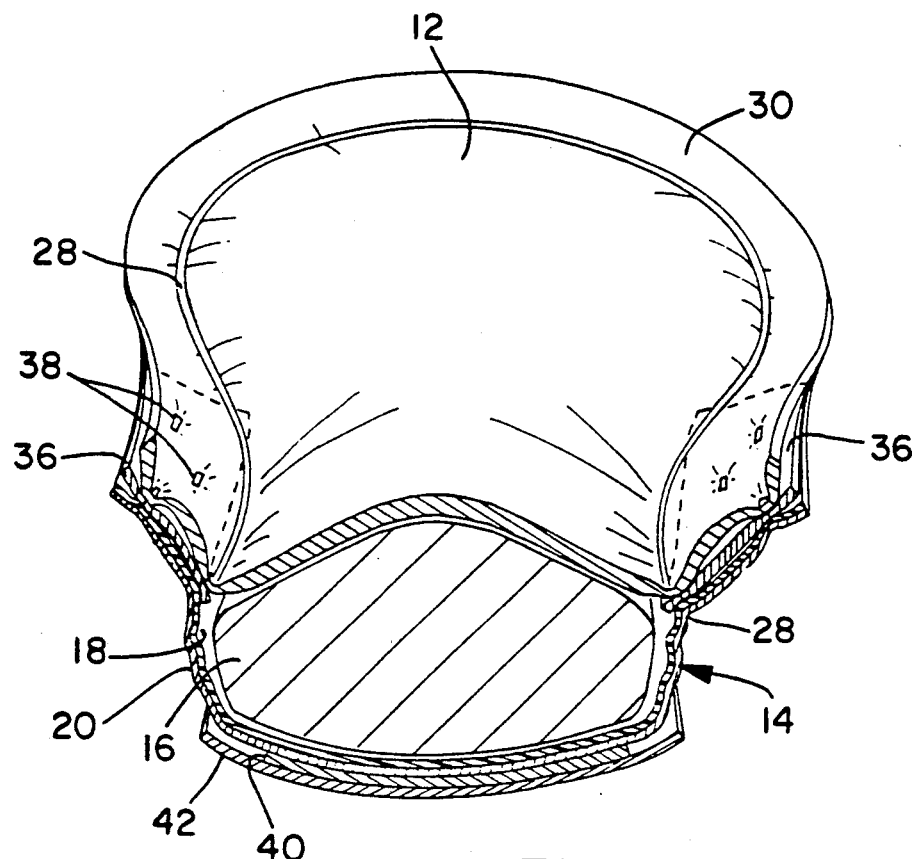
FIG. 5 is a cross-sectional view of the absorbent article taken along line 5—5 of FIG. 4.
Figure 6:
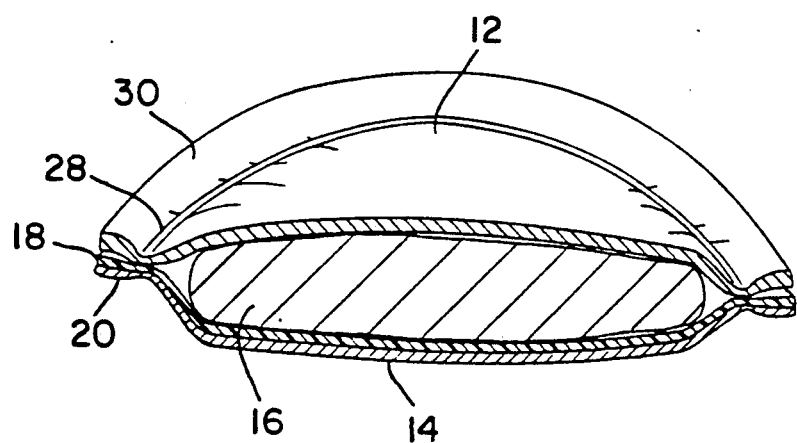
FIG. 6 is a cross-sectional view of the absorbent article taken along line 6—6 of FIG. 4.
Figure 7:
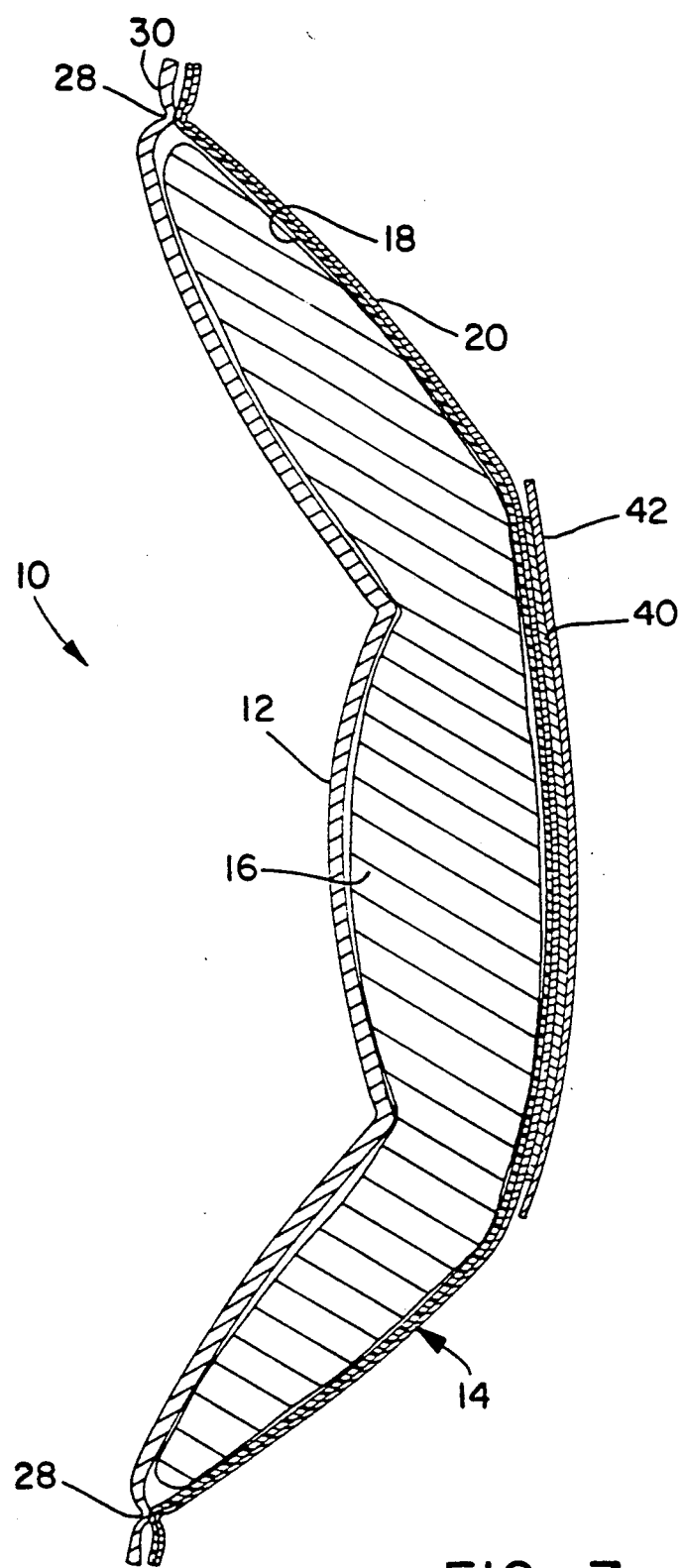
FIG. 7 is a cross-sectional view of the absorbent article taken along line 7—7 of FIG. 4.

The baffle 14 is a bicomponent structure comprised of a liquid-impermeable inner layer 18 and a cloth-like outer layer 20, see FIGS. 5–7. The inner layer 18 can be made from a polymer and be in the form of a film or sheet. Examples of useful polymers include polypropylene, polyethylene or combinations thereof. The outer layer 20 can be any nonwoven, fabric material having a smooth and soft feel to the human hand. A nonwoven synthetic material, such as spunbond, is preferred because it exhibits a cloth-like feel and is not irritating to human skin. The baffle 14 can be formed by extruding the polymer onto the spunbonded web to form an integral sheet.

The absorbent 16 can be any absorbent material that will absorb bodily exudates such as menses, blood, catamenial fluids and urine. Suitable absorbents include cellulose fluff, wood fluff, rayon and cotton. Meltblown polymers, such as polyester, polypropylene or coform can also be used. Coform is an air-formed combination of a meltblown polymer, such as polypropylene, with staple cellulose fibers. A particularly preferred material is wood fluff as it is low in cost, relatively easy to form and has good absorbency.

The absorbent 16 has an hourglass shape with two enlarged end portions 22 and 24. The end portions 22 and 24 are relatively flat with a rounded profile which are seperated by a narrow center portion 26. The center portion 26 can be thicker than the end portions 22 and 24 and is preferably about 1.75 to 3 times thicker than the end portions 22 and 24. Alternatively, the absorbent article 16 can have a uniform thickness but the center portion 26 would contain superabsorbent or be constructed of fibers having the ability to absorb a greater amount of fluid. It should be noted, that the absorbent 16 can be constructed of a single layer of absorbent material or it can be formed from two or more layers joined together. The amount of absorbent 16 within the article 10 can vary depending upon how much body fluid the product is designed to retain. A highly-absorbent material, such as a hydrogel superabsorbent, can be added to the absorbent 16 to assist in retaining the fluid.

The liner 12 and the baffle 14 are bonded together by a seal line 28 which extends around the outer periphery of the absorbent article 10. The seal line 28 can be formed at a height which is about half the vertical height of the absorbent 16 or greater, as best shown in FIGS. 5 and 6. The seal line 28 can be formed in a variety of ways, including ultrasonic sealing, heat sealing, pressure sealing or by the use of an adhesive. Ultrasonic sealing is preferred for it results in a neat line and has less of a tendency to perforate the material than does heat sealing. The sealing method should not leave a hard, uncomfortable residue that would be annoying to the wearer. Sealing about the outer periphery, on a path inward of the peripheral edge, will provide a soft decorative fringe 30. The fringe 30 can extend outward from the seal line 28 a distance from about 1/16 to ½ of an inch, preferably about ¼ of an inch. The fringe 30 provides a soft surface which contacts the wearer's body and provides a comfortable fit while the product is being worn.

A pair of walls 32 and 34 are formed on opposite sides of the center portion 26 of the absorbent 16 by sealing the liner 12 to the baffle 14 with a strip of elastic 36 sandwiched therebetween. Preferably, the liner 12 and the baffle 14 are coextensive and generally rectilinear in shape so as to have two longitudinal side edges. A strip of elastic 36 is positioned on each side of the center portion 26 adjacent to the absorbent 16. Each strip of elastic 36 extends from just inside the seal line 28 to the outer surface of each of the longitudinal side edges. The strips of elastic 36 are secured to both the liner 12 and the baffle 14 by a plurality of bond points 38. The bonds can be formed with an adhesive or by ultrasonic bonding as was explained above in reference to the seal line 28.

The elastic 36 can be made from any suitable type of elastic material and can be in the form of a single, relatively flat rectangular strip or be a plurality of individual elastic strands. The cross-sectional shape of the elastic strands can vary and may include round, oval, square, rectangular or irregular shapes. Heat-shrinkable elastics can be used and offer the advantage in that the elastic may be applied as a nonelastic film which becomes elastic upon heating. Heat-shrinkable elastics are also relatively easy to form into particular shapes by controlling the method and location of the heat source. For example, the elastic may be applied in a rectangular strip form and heat can be applied from the body-side surface of the article such that the absorbent 16 will insulate the heat-shrinkable elastic from the applied heat and permit only the area in the exposed walls to shrink. Exemplary of heat shrinkable elastics are those taught in U.S. Pat. Nos. 3,912,565, 3,819,401 and 3,639,917.

When non heat-shrinkable elastics are utilized, the elastic can be applied as elongated strips which are secured in place, for example by being sewn or by use of an adhesive, while under tension and then allowed to relax. Such materials, and processes for their application, are well known in the art.

An alternative to the use of a liquid-impermeable polymer inner layer 18, along with the elastic 36, is to use a moldable plastic foam shell. Foams can be made to be both liquid-impermeable and resilient so as to provide a soft feel to the wearer. The foam can be molded with gathers in the walls so as to allow the product to conform to the body of the wearer. Such a product would not require elastic as it would be molded in a predetermined container shape. A suitable foam material is polyethylene-polyvinyl-acetate. This material can be vacuum and thermally molded to a desired shape and then have the absorbent inserted into it before being covered by the liner. The liner can be attached to the outer periphery of the foam shell by an adhesive or by heat bonding.

The walls 32 and 34 are generally parallel to one another and the top of each wall can be about the same height as the top of the absorbent 16. It is also possible to form the absorbent 16 such that its top surface is above the height of the top edge of the walls 32 and 34, if desired. For a sanitary napkin, the preferred design is one wherein the walls 32 and 34 extend into the crease at the sides of the female genital organs or pudendum. The length of the product is designed so as to extend adequately, caudally and dorsally, to prevent leakage in those directions while snugly fitting the body. The length should not be so long as to be uncomfortable or interfer with the fit of the clothes of the wearer. While body sizes and shapes vary, it has been found that a feminine product having dimensions within a certain range performs satisfactory. Generally, the center portion 26 for a feminine product should be about 1–3 inches wide, preferably 2–3 inches wide, and may be slightly larger for incontinence devices. The length of a feminine product can vary between about 6–12 inches, while a medium size diaper or a regular size incontinent device would have a length of between about 10–30 inches. A preferred length for a feminine product is 8–9.5 inches and a preferred length for a medium size diaper or a regular size incontinent device is about 15–24 inches.

When the absorbent article 10 is a feminine product, a garment attachment adhesive 40 can be used to secure it to the exterior surface of the outer layer 20. The adhesive 40 can be in the form of a single strip or two or more spaced apart parallel strips. When the adhesive 40 is in the form of a single strip, it is preferably about 1–1.5 inches wide and about 4–6 inches long. The adhesive 40 is covered by a removeable peel strip 42 which is slightly larger in size. The peel strip 42 is designed to keep the adhesive 40 free of contaminants until the feminine product is ready to be used. At that time, the consumer removes the peel strip 42 thereby exposing the exterior surface of the adhesive 40 which will secure the feminine product to the inside of her undergarment.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An absorbent article comprising:
   (a) a liquid permeable bodyside liner;
   (b) a baffle having a liquid-impermeable inner layer and a cloth-like outer layer;
   (c) an absorbent positioned between said liner and said baffle and being enclosed therein, said absorbent having an hourglass shape with enlarged end portions seperated by a narrow center portion, said center portion being about 1.75 to 3 times thicker than said end portions; and
   (d) a pair of walls formed on opposite sides of said center portion of said absorbent by securing an elastic member between said liner and said baffle, said walls extending upward and outward from said center portion and being seperated by a distance approximately equal to the width of one of said end portions.

2. The absorbent article of claim 1 wherein said inner layer of said baffle is a polymer and said outer layer is a nonwoven web.

3. The absorbent article of claim 2 wherein said outer layer is a spunbonded web having a cloth-like feel.

4. The absorbent article of claim 2 wherein said inner and outer layers of said baffle are formed as an integral sheet.

5. The absorbent article of claim 1 wherein said inner layer of said baffle is polypropylene and said outer layer is a nonwoven fabric material.

6. The absorbent article of claim 1 wherein said inner layer of said baffle is polyethylene and said outer layer is a nonwoven fabric material.

7. The absorbent article of claim 1 wherein said inner layer of said baffle is a combination of polypropylene and polyethylene and said outer layer is a spunbonded web.

8. A three-dimensional shaped absorbent article comprising:
   (a) a liquid permeable liner designed to be positioned adjacent to a human body;
   (b) a baffle being generally coextensive with said liner and having a liquid-impermeable inner layer and a cloth-like outer layer;
   (c) an absorbent positioned between said liner and said baffle and being enclosed therein by bonding said baffle to said liner, said absorbent having an hourglass shape with enlarged end portions seperated by a narrow center portion, said center portion being about 1.75 to 3 times thicker than said end portions; and
   (d) a pair of generally parallel walls formed on opposite sides of said center portion of said absorbent by securing a strip of elastic between said liner and said baffle, said walls extending upward and outward from said center portion and being seperated by a distance approximately equal to the width of one of said end portions.

9. The absorbent article of claim 8 wherein said inner layer of said baffle is a polymer and said outer layer is a nonwoven web.

10. The absorbent article of claim 9 wherein said outer layer is a spunbonded web having a cloth-like feel.

11. The absorbent article of claim 9 wherein said inner and outer layers of said baffle are formed as an integral sheet.

12. The absorbent article of claim 8 wherein said inner layer of said baffle is polypropylene and said outer layer is a nonwoven fabric material.

13. The absorbent article of claim 8 wherein said inner layer of said baffle is polyethylene and said outer layer is a nonwoven fabric material.

14. The absorbent article of claim 8 wherein said inner layer of said baffle is a combination of polypropylene and polyethylene and said outer layer is a spunbonded web.

* * * * *